(12) United States Patent
Blair et al.

(10) Patent No.: US 9,526,459 B2
(45) Date of Patent: Dec. 27, 2016

(54) MEDICAL DEVICE VISUAL MANAGEMENT SYSTEM AND METHOD

(71) Applicant: General Electric Company, Schenectady, NY (US)

(72) Inventors: David Michael Blair, Columbia, MD (US); Lawrence Guy Ten Eyck, Ellicott City, MD (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 89 days.

(21) Appl. No.: 14/143,368

(22) Filed: Dec. 30, 2013

(65) Prior Publication Data

US 2015/0187196 A1    Jul. 2, 2015

(51) Int. Cl.

| | | |
|---|---|---|
| G08B 21/02 | (2006.01) | |
| A61B 5/00 | (2006.01) | |
| G08B 5/36 | (2006.01) | |
| A61B 5/0205 | (2006.01) | |
| G06F 19/00 | (2011.01) | |
| A61G 11/00 | (2006.01) | |

(52) U.S. Cl.
CPC ............... *A61B 5/74* (2013.01); *A61B 5/0205* (2013.01); *G06F 19/3406* (2013.01); *G08B 5/36* (2013.01); *A61G 11/00* (2013.01); *A61G 11/009* (2013.01); *A61G 2203/20* (2013.01); *A61G 2203/46* (2013.01); *A61G 2210/90* (2013.01)

(58) Field of Classification Search
CPC ... A61B 5/0002; A61B 5/0008; A61B 5/0013; A61B 1/00009; A61B 6/461; A61B 6/563; A61B 5/74; G06F 19/321; G06F 19/3418; G06F 19/345; G08B 21/02; G08F 19/3406
USPC ...... 340/539.12, 573.1, 691.6; 600/300, 301, 600/476, 558, 559, 587; 128/903, 904
See application file for complete search history.

(56) References Cited

U.S. PATENT DOCUMENTS

| | | | |
|---|---|---|---|
| 2003/0193566 A1* | 10/2003 | Matsuda et al. | 348/189 |
| 2004/0234254 A1* | 11/2004 | Czupich et al. | 392/403 |
| 2007/0192134 A1* | 8/2007 | Littenberg et al. | 705/2 |
| 2009/0181645 A1* | 7/2009 | Chan et al. | 455/412.1 |
| 2009/0192541 A1* | 7/2009 | Ortiz et al. | 606/192 |
| 2010/0222649 A1* | 9/2010 | Schoenberg | 600/301 |
| 2010/0305467 A1* | 12/2010 | Rodilla Sala et al. | 600/546 |
| 2013/0063646 A1* | 3/2013 | Ueno et al. | 348/333.1 |
| 2013/0245458 A1* | 9/2013 | Spector | 600/476 |
| 2013/0286364 A1* | 10/2013 | Sung et al. | 353/119 |

* cited by examiner

Primary Examiner — Hung T Nguyen

(57) ABSTRACT

A visual management system for a medical device, the system comprises a projection device and a controller to generate control signals based upon parameters associated with use of the medical device. The projection device projects a message onto a surface, upon which the image is viewable, in response to the control signals.

29 Claims, 6 Drawing Sheets

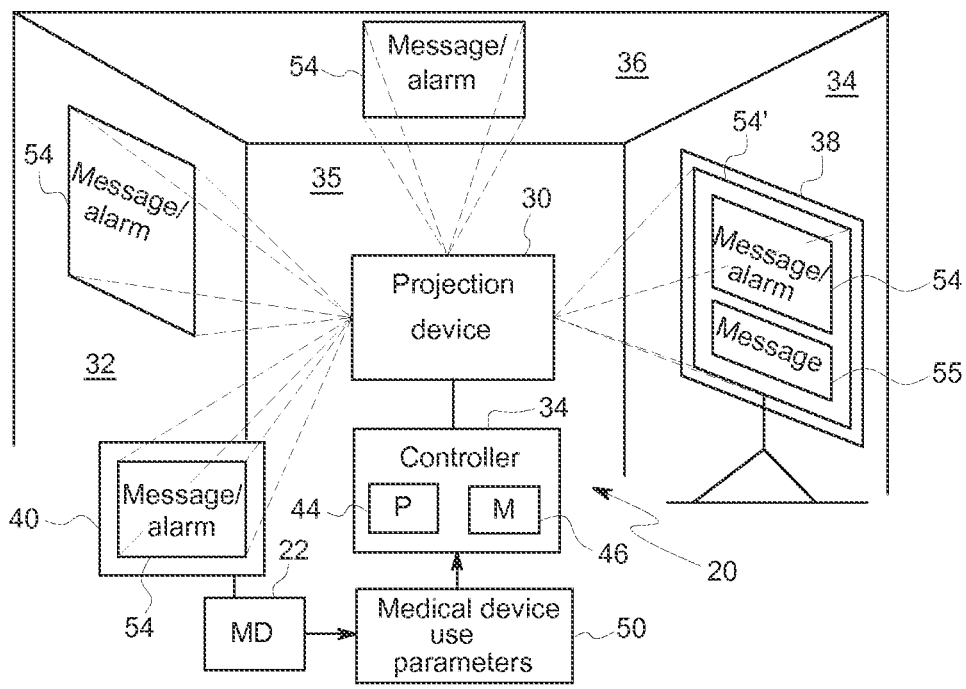
FIG. 1
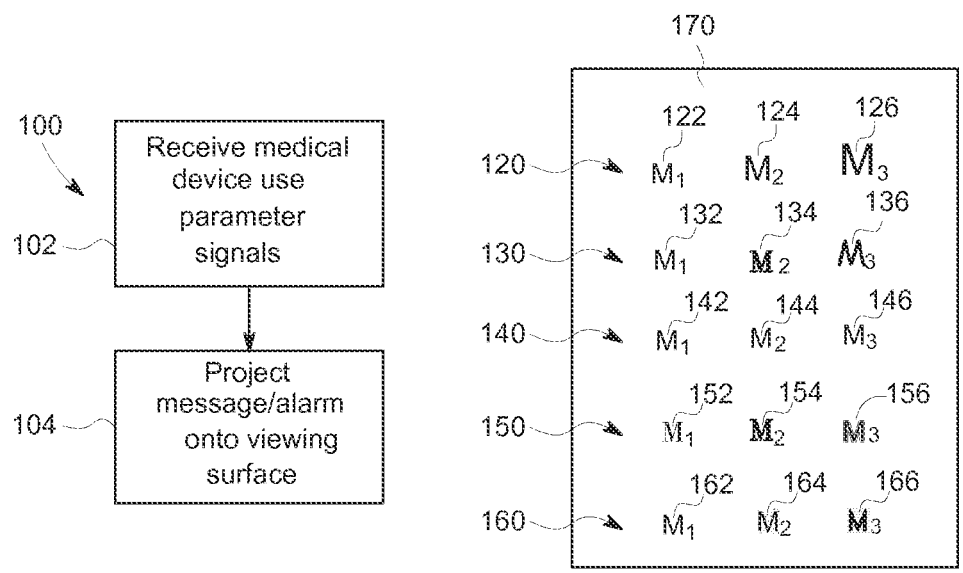
FIG. 2
FIG. 3

MEDICAL DEVICE VISUAL MANAGEMENT SYSTEM AND METHOD

BACKGROUND

Medical devices often display information using a display monitor such as an LCD or LED display screen. Information presented by the display screen is sometimes difficult to read or appreciate. Some medical devices additionally output an audible alarm to notify a care person of an alert condition. Such audible alarms may contribute to undesirable noise levels.

BRIEF DESCRIPTION OF THE DRAWINGS

FIG. 1 is a schematic diagram of an example medical device visual management system.

FIG. 2 is a flow diagram of an example method that may be carried out by the system of FIG. 1.

FIG. 3 is a schematic diagram of an example schemes for communicating an importance or priority of a message being projected by the system of FIG. 1.

DETAILED DESCRIPTION OF THE EXAMPLE EMBODIMENTS

Figure 4:
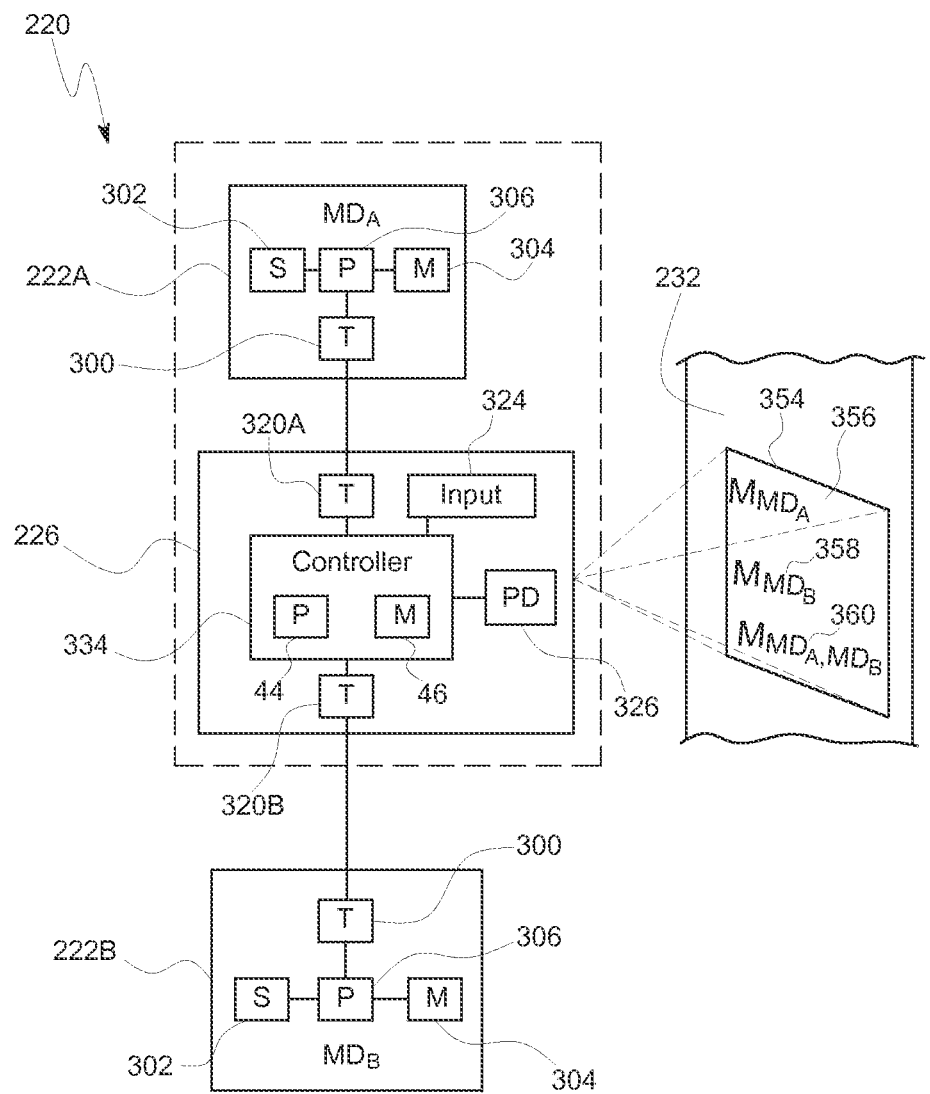
FIG. 4 is a schematic diagram of another example medical device visual management system.

FIG. 1 schematically illustrates an example visual management system 20 for a medical device 22. As will be described hereafter, visual management system 20 projects data, notifications, instructions and/or alarms (collectively referred to as a "message" or "messages") onto a surface, providing the message on a surface remote from the medical device and/or in an enlarged format. As a result, the message is more readily viewed, more readily read and more readily appreciated. At the same time, the message does not contribute to undesirable level of noise in a patient care facility.

As shown by FIG. 1, visual management system 20 comprises projection device 30 and controller 34. Projection device 30 comprises an electronic device configured to receive signals representing a message and to project light or other electromagnetic radiation onto a projection surface to form an image of the message on the projection surface. In one implementation, projection device 30 comprises a front projection device. In one implementation, projection device 30 is configured to project the image through air external to the medical device onto a projection surface. In one implementation, projection device 30 is configured to project the image onto an at least partially reflective surface upon which the image is viewed. In one implementation, projection device 30 projects an image through air external to the medical device or through air within an incubator or warmer chamber onto a surface that comprises pixel elements (such as phosphor elements) that become excited and viewable in response to being impinged by the light or electromagnetic radiation projected in the form of the image. In one implementation, projection device 30 is configured to project an image of the projection onto one or more selectable projection surfaces such as different walls 32, 34, 35 of a room, a ceiling 36 of a room, a projection panel or screen 38 independent of the medical device or a projection panel or screen 40 provided by, supported by and/or carried by the medical device 22.

In one implementation, projection device 30 is provided as part of the same medical device 22 providing screen 40. In such an implementation, projection device 30 is spaced from screen 40. For example, in one implementation, medical device 22 comprises an incubator or warmer having a pair spaced vertical rails at its head, wherein the rails vertically support a canopy or overhead heating element. In such an implementation, screen 40 extends between and is supported by the pair of spaced vertically extending rails. In one implementation, projection device 30 is spaced from screen 40 by being supported at a foot of the incubator or warmer or has a projection element cantilevered from or extending from the head while being aimed at screen 40. In one implementation, panel or screen 40 is sized to fit the through a doorway during transportation or is otherwise retractable (such as being configured to be wound or unwound), foldable or collapsible to be fit through a doorway. In such an implementation, because screen 40 is carried by or is provided as part of medical device 22 and is sized to fit through a doorway, system to 20 accommodates rooms are neonatal intensive care units with limited or no available wall space and provides a means to continue visual monitoring during transportation of the patient to new locations or alternative care areas, like X ray or the operating theatre.

Figure 8:
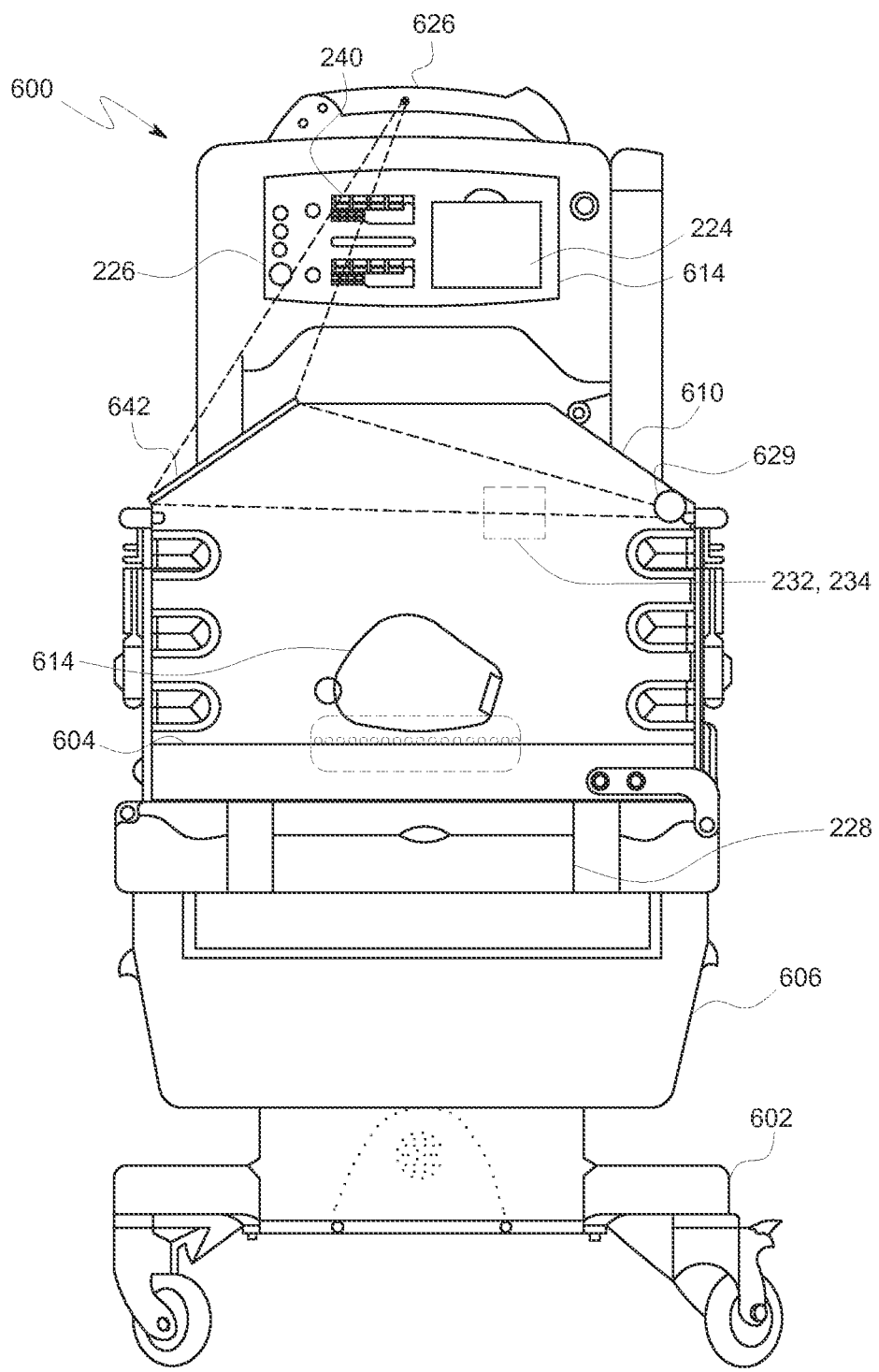
FIG. 8 is a front view of the system of FIG. 6.

In yet another implementation, projection device 30 is supported in carried by a first medical device while being configured to project the message onto a projection surface supported or provided by another medical device 22. For example, in one implementation, projection surface 38 is supported and carried by vertically extending rails at the head of an infant incubator or warmer, examples of which are shown in FIG. 8. In one implementation, projection surface 38 may be provided on a backside of such rails. In one implementation, the projection surface 38 provided by the other medical device 22 is sized to fit through a doorway or is retractable, collapsible or foldable to fit through a doorway.

In yet another implementation, projection device 30 is configured to project the message onto a projection surface 40 which is provided by one of more walls of an infant incubator or infant warmer chamber that surround the mattress or bed of the infant incubator or warmer. For example, in one implementation, one or more of the walls may include a retainer, such as a clip or pair of card receiving channels, for retaining a reflective or opaque sheet, panel or the like, allowing the reflective or opaque sheet, panel or the like to be inserted for use as projection surface 40 while also allowing removal to increase visibility of the one or more patients within such walls. In another implementation, walls themselves may be configured to be partially transparent while also allowing viewing of the message that is projected onto such walls. In such an implementation, the care person has access to the message and all of the projected information while working on the patient in the warmer or incubator. Such an implementation of system 20 facilitates the performance of surgical procedures in the bed of the warmer or incubator in circumstances where a physician cannot afford to raise his or her head to look at data displays.

In one implementation, projection device 30 may comprise multiple projection lenses through which the light is projected onto the different selectable projection surfaces. In another implementation, projection device 30 may comprise a projection lens that pivots, slides or otherwise moves to alter the angle at which the light is projected and to alter the surface upon which the image of the message is projected. In one implementation, projection device 30 is configured to concurrently project a message through air external to the medical device onto multiple distinct surfaces or to concurrently project different messages onto different surfaces.

Controller 34 comprises one or more processing units configured to generate control signals causing projection device 30 to project the one of more images onto the one or more projection surfaces 32, 34, 36, 38, 40. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other non-transitory persistent storage. In other embodiments, hard wired circuitry may be used in place of or in combination with software instructions to implement the functions described. For example, controller 34 may be embodied as part of one or more application-specific integrated circuits (ASICs). Unless otherwise specifically noted, the controller is not limited to any specific combination of hardware circuitry and software, nor to any particular source for the instructions executed by the processing unit. In the example illustrated, controller 34 comprises processing unit 44 and memory 46.

Processing unit 44 carries out the instructions provided in memory 46 for controlling at least projection device 30. Memory 46 comprises a non-transitory computer-readable medium containing software, circuitry or code for directing processing unit 44 to carry out method 100 illustrated in FIG. 2. As indicated by step 102 of method 100 and FIG. 2, processing unit 44, following instructions contained in memory 46, receives or otherwise obtains signals representing or indicating one or more parameters 50 (schematically represented in FIG. 1).

Parameters 50 comprise values associated with the use of medical device 22. In one implementation, parameters 50 comprise values that are sensed during the use of medical device 22. Examples of such sensed parameters include, but are not limited to, sensed physiological conditions regarding one or more patients, sensed environmental conditions such as humidity, temperature and the like and/or sensed properties of the medical device itself such as a frequency at which a portion of the medical device operates, a temperature of the medical device itself and the like.

In one implementation, parameters 50 comprise current and/or programmed future operational settings or operational characteristics of medical device 22. Such settings or operational characteristics of medical device 22 may be retrieved from a memory associated with medical device 22. Examples of settings or operational characteristics of medical device 22 include, but are not limited to, the input rate at which the medical devices to operate, the humidity setting, a temperature setting and the like.

In one implementation, parameters 50 comprise stored values pertaining to the one or more patients using medical device 22. For example, parameters 50 may comprise a patient's age, weight, particular health conditions and the like. In one implementation, controller 34 receives multiple medical device use parameters including each of sensed values, medical device operational characteristics are settings and patient characteristics.

As indicated by step 104 of method 100, processing unit 44, following instructions contained memory 46, generates control signals based upon parameters 50 so as to cause projection device 30 to project a message through the air external to medical device 22 and onto a projection surface 32, 34, 35, 36, 38, 40. In one implementation, the control signals generated by processing unit 44 cause projection device 30 to project an image of the actual parameters 50 received from medical device 22. In another implementation, processing unit 44, following instructions contained memory 46, analyzes one or more of the parameters 50 received from medical device 22 to determine the content and/or characteristics of the message to be projected or to determine whether a message should be projected at all. In one implementation, the content is not the actual parameters themselves, but is content that is derived from and based upon the actual parameters.

In one implementation, processing unit 44 may compare one or more of the parameters to one or more thresholds or other criteria when determining whether a message should be presented, when determining the priority or importance of the message or when determining the content of the message. For example, depending upon extent to which a parameter value exceeds or falls short of a threshold, processing unit 44 may generate control signals causing projection device 30 to project a message comprising a stern alarm in one circumstance or to project a caution notification in another circumstance. In another circumstance, based upon the received parameters from medical device 22, processing unit 44 may determine that a message should not be presented. Because processing unit 44 may determine to refrain from projecting a message based upon received parameters from medical device 22, system 20 avoids projecting unnecessary or less important data or notifications, avoiding visual clutter and reducing the likelihood that they care person or physician will inadvertently or mistakenly disregard or overlook a critical or important message, such as an alarm notification.

In one implementation, processing unit 44 may generate control signals causing projection device 30 to additionally or alternatively project information that accompanies an alarm portion of the message or that is projected independent of an alarm notification. In one operational mode, such additional information may indicate when a concerning situation or problem is anticipated or expected to occur in the future. In another operational mode, such additional information may comprise a suggestion, recommendation or instruction including one or more steps, procedures or actions to be taken by a physician or care person either to address or remedy a current or ongoing concern regarding the use of medical device 22 or to prevent or mitigate a future anticipated problem or concern regarding the use of medical device 22. Such instruction may involve an adjustment or modification of operational characteristics of medical device 22, the supply of evaporate, fluids or other resources for medical device 22, or changes with respect to the patient being served by medical device 22.

As shown by FIG. 1, because message 54 is projected onto projection surfaces 32, 34, 38 and 40, message 54 is larger than what can be displayed on a display screen of medical device 22 itself. The size of message 54 is enlarged such that it is more conspicuous, easier to view, and easier to read. The large size of message 54 may additionally allow a greater amount of information to be presented. At the same time, visual management system 20 provides such a larger message 54 without correspondingly increasing the cost of medical device 22 with enlarged display screens.

In one implementation, message 54 comprises alphanumeric symbols or characters providing an alert, notification or additional information. Each individual alphanumeric character has a character size of at least 1 inch, wherein the size of a character is the measured from two outer most edges of the character that are separated by the greatest distance. In one implementation, each individual alphanumeric character has a character size of at least 3 inches. As a result, message 54 may be viewed from a distance of greater than 6 feet, such as from across a room.

In addition to increasing the size of message 54, visual management system 20 provides message 54 upon a projection surface 32, 34, 35, 36, 38 that is distant or remote from medical device 22. As a result, a physician or care person may view message 54 at additional locations within a room, such as an infant nursery, when the physician or care person is not necessarily adjacent medical device 22. In addition, the physician or care person may view the message 54 at a greater number of angles or positions relative to medical device 22, allowing the physician or care person to monitor the use of medical device 22 (and possibly another medical device proximate the physician or care person) from a single location or while involved with a healthcare task not associated with and remote from medical device 22.

In one implementation or selectable mode, projection device 30 further allows the operator, physician or care person to input or enter a selection through an input device to system 20 selecting which of projection surfaces 32, 34, 36, 38 and 40 are to receive message 54 or various portions of message 54. For example, in one implementation, controller 34 is operable in a mode in which projection device 30 projects message 54 of projection surface 32 and projects a larger message 54' which includes both message 54 as well as additional message content 55. In such a mode, more detailed information or content is provided on display surface 38 while boiled down, filtered or critical information is presented as part of message 54 on projection surface 32. As a result, visual management system 20 allows a physician or care person to select which projection surfaces are to receive larger amounts of content in which projection surfaces are to receive more concise, possibly more critical, content. The selection of such projection surfaces and what content or messages are to be presented on such projection surfaces may be based upon the available surface area or size of the different projection surfaces and/or different viewing characteristics associated with each of the selectable projection surfaces. For example, a first wall may be more cluttered and may be less usable as a projection surface while a second different wall may have a greater available surface area or may be more easily viewed from throughout a room or through a viewing window from a hall outside the room.

In one implementation, medical device 22 may itself include a display screen, wherein controller 34 generates control signals such that the display screen of medical device 22 presents the greater content message 54' while the more critical concise message 54 is projected onto one of the projection surfaces. In one implementation, memory 46 comprises instructions for directing processing unit 44 of controller 34 to present a greater content message on the display screen of medical device 22 and to only project the more concise content message 54 when warranted, such as when an alarm or urgent notification condition exists. In such a mode, because the projection surface does not always have a projected message thereon, when projection service does have a projected message, the physician or caretaker may be more likely to notice and pay attention to the message being projected on the projection surface.

In one implementation, controller 34 provides a care person or physician with the option of selecting one or more modes by which non-textual attributes of a message may be varied to communicate the importance of a message. The term "non-textual attributes" refers to attributes that are independent of the alphanumeric character or string of alphanumeric characters. For example, two identical words may have the exact same text or the exact same string of alphanumeric characters, however such words may differ from one another by having different non-textual attributes such as size, font, color, brightness, display frequency and the like. In one implementation, controller 34 may receive such a selection through an input device such as a keyboard, touch screen, mouse and the like.

FIG. 3 illustrates various examples of rows of selectable schemes or modes 120, 130, 140, 150 and 160 by which the same message may be projected in different fashions (with different non-textual attributes) to communicate a priority or importance of the projected messages M. In the example illustrated, each message M has an identical string of alphanumeric characters or symbols, wherein each identical string has different non-textual attributes. In mode 120, the importance of the particular message M is communicated by varying the size of the projected message on the projection surface 170. In the example illustrated, message 122 is smaller than message 124 which is smaller than message 126, wherein the increased importance or priority of messages 122, 24 126 is represented by a larger size of the projected images. The larger size also serves to increase the notice ability of the more important message 126.

In mode 130, the importance of the particular message M is communicated by varying the font of the projected message, wherein message 132 is projected in a font different than that of message 134 which is different than that of message 136 and wherein the font chosen for message 136 is associated with a higher importance or criticality or is more noticeable as compared to the font of projected images 132 and 134.

In mode 140, the importance of the message M is communicated by varying the color of the projected message. For example, in one implementation, message 142 is projected in a green color indicating less importance, message 144 is projected in a yellow color indicating greater importance and message 146 is projected in a red color indicating the highest degree of importance or priority.

In mode 150, the importance of message M is communicated by varying the frequency at which the messages flashed or presented upon the projection surface. For example, in one implementation, message 152 is projected at a first frequency, message 154 is projected a second frequency greater than the first frequency and message 156 is projected at a third frequency greater than the second frequency, wherein an increase frequency of message 156 indicate that message 156 is more important. In other implementations, greater importance of a message may be indicated by a reduced frequency.

In mode 160, the importance of a message is communicated by varying a brightness of the projected message M. In the example illustrated, message 162 has a first brightness, message 164 has a second brightness greater than the first brightness and method 166 has a third brightness greater than the second brightness. In one implementation, the greater brightness indicates a greater importance or criticality for the message, increasing a likelihood the message will be noticed and acted upon.

FIG. 4 schematically illustrates visual management system 220, an example implementation of visual management system 20. Visual management system 220 manages and presents messages from multiple medical devices. In one implementation, visual management system 220 manages and presents messages from multiple independently operating medical devices. In one implementation, visual management system 220 manages and presents messages for multiple independently operating medical devices that are being utilized by different patients.

Visual management system 220 comprises medical device (MDA) 222A, medical device 222B (MDB) and message manager 226. Medical devices 222A and 222B (collectively referred to as medical devices 222) treat or service one or more patients. In one implementation, medical devices 222 treat different patients. In another implementation of medical devices 222 comprise distinct medical devices that treat a single common patient. In one implementation, medical devices 222 are of the same type of medical device. For example, in one implementation, medical devices 222 may comprise infant care stations such as an incubator or warmer. In another implementation, medical devices 222 may be substantially identical to one another such as where medical devices 222 comprise the same model of a particular type of medical device. In yet other implementations, medical devices 222 may comprise different medical devices that perform different functions with respect to the same patient or different patients. In some implementations, medical device 222B is made or sold by a different entity that the entity that made or sold device 222A and/or message manager 226, wherein device 222B is provided with authorization (such as through a license) to communicate with and utilize the projection capabilities of message manager 226. Examples of medical devices 222 include, but are not limited to, infant care stations, incubators, warmers, ancillary devices (physiologic monitor, ventilator, pulse oximeter, infusion pump and/or other electronic devices) used in the care of the patient which, may be attached to the incubator or warmer's visual management system connected directly through the incubator or warmer connection port or directly connected to a free standing visual management system, whereby ancillary device alerts, alarms and messages for correcting operational parameters are offered to the care person. In other implementations, medical device 222 may comprise other types of medical devices, whether used in a residential or assisted care environment, a clinical environment or a hospital environment.

In the example illustrated, each of medical devices 222 comprises transceiver 300, sensors 302, memory 304 and a microprocessor or processing unit 306. Each of transceivers 300 comprises a device to send and/or receive signals carrying or representing parameters 50 (described above) associated with the use of the particular medical device 222A, 222B. In one implementation, transceivers 300 are configured to directly transmit signals to manager 226 in a wired or wireless fashion. In one implementation, transceivers 300 may transmit such signals in a wireless fashion using radio frequency signals, infrared signals or other wireless carriers. In yet other implementations, transceivers 300 are configured to indirectly transmit signals or information to manager 226 through an intermediary. For example, transceivers 300 may transmit signals to manager 226 across a local area network or across a wide area network such as the Internet.

Sensors 302 comprise one or more sensing devices associated with each of medical devices 222 that detect environmental conditions such as (A) temperature, humidity and the like, (B) patient or physiological conditions and/or (C) medical device operational values or conditions such as a frequency at which a portion of the medical device operates, a temperature of the medical device itself and the like. In one implementation, each medical devices 222 operates independent of one another. In another implementation, one of medical devices 222 is ancillary to the other of medical devices 222, providing supplemental monitoring of functioning which assists the functioning of the other of medical devices 222. In one implementation, signals from sensors 302 are transmitted to message manager 226. In one implementation, signals from sensors 302 are filtered, analyzed or processed by processor 306 of the associated medical device 222A, 222B prior to being transmitted to manager 226. In one implementation, signals from sensor 302 are utilized by processor 306 of the associated medical device 222A, 222B to generate signals distinct from the signals received from sensor 302, wherein the newly generated distinct signals are transmitted to manager 226. For example, in one implementation, one or multiple medical devices 222 may analyze its own sensed data to identify a condition warranting the projection of a message such as a notification or alert, (1) wherein the signals transmitted to manager 226 provide the message to be projected or (2) wherein the signals are utilized by manager 226 to present a message, but comprise an abstraction of the sensed parameters or a result/conclusion computed or derived by processing unit 306 from the sensed parameters. In one implementation, processor 44 of message manager 226 interprets and derives new values, alerts/alarms or messages from the multiple medical devices 222, where the sensed data, when combined may result in a more important alert and or alarm. For example, in one implementation, one of medical devices 222 comprises a physiologic monitor recording respiratory rate and heart rate while another medical device 222 comprises a pulse oximeter detecting % saturation of the blood. In such an implementation, message manager is configured to generate a message based on inputs from both devices, respiratory rate, heart rate and % saturation of the blood, wherein such inputs or sensed parameters, when collectively analyzed, may be predictive of impending respiratory arrest, a condition which may not be as readily detected by looking at single physiologic variable alone.

Each of memories 304 comprises a non-transitory computer-readable medium which stores computer-readable instruction or code/software for directing the operation of processing unit 306. In one implementation, each of memories 304 further stores parameters 50 comprising user/care person/physician entered or manufacturer default operational settings for the operation of the particular medical device 222. In one implementation, processing unit 306 identifies the current operational setting in use by the medical device 222 and transmits signals indicating the current operational setting that is being used to message manager 226. In another implementation, processing unit 306, following instructions contained a memory 304, derives other values based upon the current operational settings and transmits signals representing the derived values to message manager 226. Examples of settings or operational characteristics of medical device 22 include, but are not limited to, the input rate at which the medical devices to operate, the humidity setting, a temperature setting and the like.

In one implementation, memory 304 may store parameters 50 which comprise values pertaining to the one or more patients using medical device 222. For example, parameters 50 may comprise a patient's age, weight, particular health conditions and the like. In one implementation, each medical device 222 transmits signals representing each of visual management system sensed values, medical device operational characteristics or settings and/or patient characteristics to manager 226.

Message manager 226 receives medical device use parameter signals (which may correspond to the actual sensed or actual stored parameter values or which may correspond to values derived from the actual sensed or stored parameter values) from each of medical devices 222 and projects one or more messages through air external to the medical devices 222 and onto a projection surface 232. In the example illustrated, message manager 226 comprises transceivers 320A, 320B (collectively referred to as transceivers 320, input 324, projection device 326 and controller 334. Transceivers 320 comprise communication devices to send and receive signals to and from transceivers 300 of medical devices 222. Although manager 226 is illustrated as having two transceivers 320 with each of transceivers 320 dedicated for communicating with an assigned one of medical devices 222, in other implementations, manager 226 may comprise a single transceiver that provides communication with each of the plurality of medical devices 222. Transceivers 320 are configured to directly communicate signals to and from medical devices 222 in a wired or wireless fashion. In one implementation, transceivers 320 may communicate such signals in a wireless fashion using radio frequency signals, infrared signals or other wireless carriers. In yet other implementations, transceivers 320 are configured to indirectly transmit and receive signals or information to and from managed medical devices 222 through an intermediary. For example, transceivers 320 may send and receive signals to and from medical devices 222 across a local area network or across a wide area network such as the Internet.

Input 324 comprise a device by which a physician, care person or other user may enter or input commands, selections and/or data for use by message manager 226. For example, input 324 may facilitate the input of a selected mode of operation for message manager 226. Examples of different modes of operation or message manager settings that are selectable by a person include, but are not limited to, (1) predefined limits or thresholds at which the projection of messages onto a remote projection surface are triggered; (2) onto what projection surface a message should be projected; (3) what types of messages are to be projected onto each of the different available projection surfaces available to projector 326; (4) the size, font, color, flash or display frequency, or brightness of a message; and (5) the particular priority or importance identifying scheme to be used, such as which of the example modes or schemes shown in FIG. 3 are to be employed. Examples of input 324 include, but are not limited to, a keyboard, a touchscreen, a touchpad, a keypad, a series of toggle or slider switches, a microphone and associated speech recognition, and a mouse in combination with displayed graphical user interfaces. In some implementations, input 324 may be provided by input components of a portable electronic device (such as a smart phone, tablet, personal data assistant or the like) independent of manager 226 which communicates with manager 226 through one of transmitters 320.

Projection device 326 is similar to projection device 30 described above. As shown by FIG. 4, projection device 326 is configured to project at least one image of at least one message 354 onto at least one projection surface 232. In some implementations, message manager 226 may control a plurality of projection devices 326.

Controller 334 is similar to controller 34 described above in that controller comprises processing unit 44 and memory 46, also described above. Controller 334 is configured carry out method 100 shown and described above with respect to FIG. 2. Controller 334 is operable in one of a plurality of different user selectable modes selectable via input 324. In the example illustrated, controller 334 is operable in a multi-manage mode in which controller 334 manages the projection of messages based upon parameters 50 (described above) associated with the use of multiple medical devices, such as medical devices 222. When in the user selected multi-manage mode, processing unit 44, following instructions provided by memory 46, receives signals corresponding to parameters 50 or derived from parameters 50 from each of multiple medical devices 222. Based upon the received signals, which are based upon parameters 50, processing unit 44, following instructions contained memory 46, generates control signals causing projection device 326 to project message 354. Message 354 comprises content based upon signals received from each of medical devices 222 or least a plurality of medical devices 222. In the example illustrated, message 354 comprises a first message segment or portion 356 (symbolically represented by $M_{MDA}$) based on parameters associated with the use of medical device 222A independent of parameters associated with other medical devices, a second message segment or portion 358 (symbolically represented by $M_{MDB}$) based on parameters associated with the use of medical device 222B independent of parameters associated with other medical devices, and a third message segment or portion 360 based upon parameters 50 associated with the use of two or more of medical devices 222. In one implementation, message portion 360 provides content that is equally applicable to each of medical devices 222. By presenting a single message portion that applies to both or a plurality of medical devices 222 rather than projecting redundant content for each medical devices 222, manager 226 reduces data clutter, creating additional rejection surface space for additional projected content or improving the conspicuousness of important content being projected.

In one implementation, message portion 360 provides content that is derived from parameters 50 from the multiple medical devices 222. For example, in one mode of operation, message portion 360 aggregates values from medical devices 222 and provides a summary of the overall operation of the two or more medical devices 222.

In one implementation, message manager 226 is distant or remote from each of medical devices 222. In another implementation, as indicated by broken lines, message manager 226 is incorporated as part of, enclosed within the same general medical device housing and/or configured to share a common memory and/or a common processing unit with medical device 222A. In those implementations in which message manager 226 is incorporated as part of, enclosed within or shares a common memory and/or common processing unit with medical device 222A, redundant components or unnecessary components may be omitted. For example, if a processing unit or memory are shared by manager 226 and medical device 222A, the redundant processing unit or memory illustrating FIG. 4 may be omitted. Redundant inputs may also be omitted. Moreover, transmitter 300 of medical device 222A may be omitted.

Figure 5:
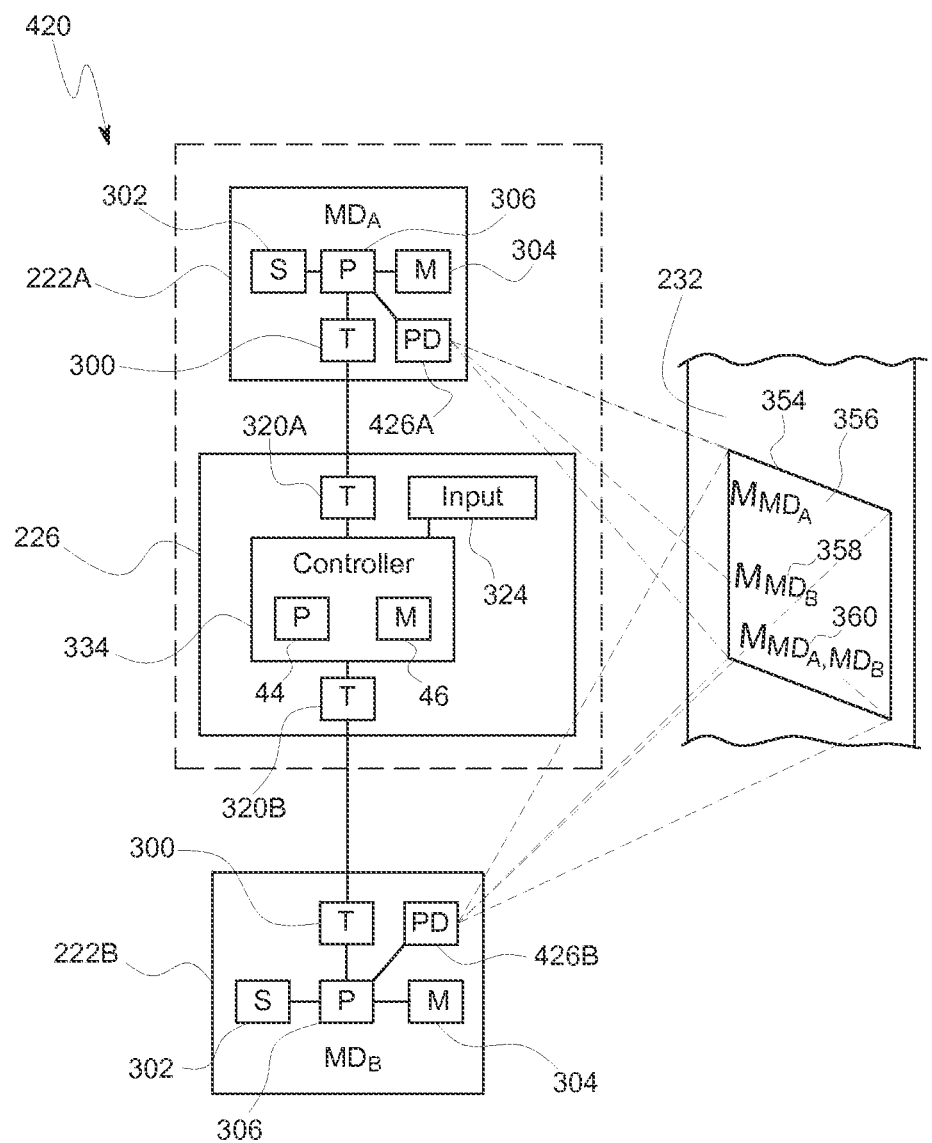
FIG. 5 is a schematic diagram of another example medical device visual management system.

FIG. 5 schematically illustrates visual management system 420, another example implementation of visual management system 20. Visual management system 420 is similar to visual management system 220 except that message manager 226 omits projection device 326 and instead utilizes projection devices 426A and 426B provided by medical devices 222A and 222B, respectively. Those remaining components of system 420 which correspond to components of system 220 are numbered similarly. As shown by FIG. 5, message manager 226 generates control signals based upon signals received from medical devices 222 based upon parameters 50 associated with the use of medical devices 222. The control signals generated by message manager 226 direct projection devices 426A and 426B to cooperate with one another to project a single image 354 including content, such as message portions 356, 358 and 360, based upon parameters associated with the use of each of medical devices 222. In one implementation or selectable mode of operation, manager 226 generates control signals such that projection device 426A project a first piece or region of message 354 while projection device 426B concurrently projects a second piece or region of message 354.

In one implementation or selectable mode of operation, controller 334 of manager 226 is configured to generate control signals such that projection device 426A projects the entirety of image 354 in circumstances where projection device will 426B is inoperative, and vice versa, providing enhanced failure redundancy. In such a circumstance, the projection device of one of medical devices 222 may project a message that is only relevant to the other of medical devices 222. In implementations where a projection surface is not sufficiently large to receive all the content of a message, message manager 226 may be operable in a mode that partitions the message such that projection device 426A project a first segment or piece of a message on a first projection surface while projection device 426B projects a second segment or piece of the message on a second projection surface, such as on a different wall.

In one implementation or selectable mode of operation, message manager 226 manages the selective use of projection devices 426A and 426B provided by different medical devices 222 to project different messages on different projection surfaces without necessarily requiring adjustment of the projection direction of either the projection devices 426. For example, a physician, care person or other user may desire to have system 420 project more important messages on a first projection surface and to project less important messages on a second projection surface. In such a scenario, message manager 226, based on the determined importance of a message, generates first control signals causing the particular projection device 426 aimed at the first projection surface to project messages, pertaining to either or both of medical devices 222, and second control signals causing the particular projection device aimed at the second projection surface to project messages, pertaining to either or both of the devices 222, that are determined to be less important.

Figure 6:
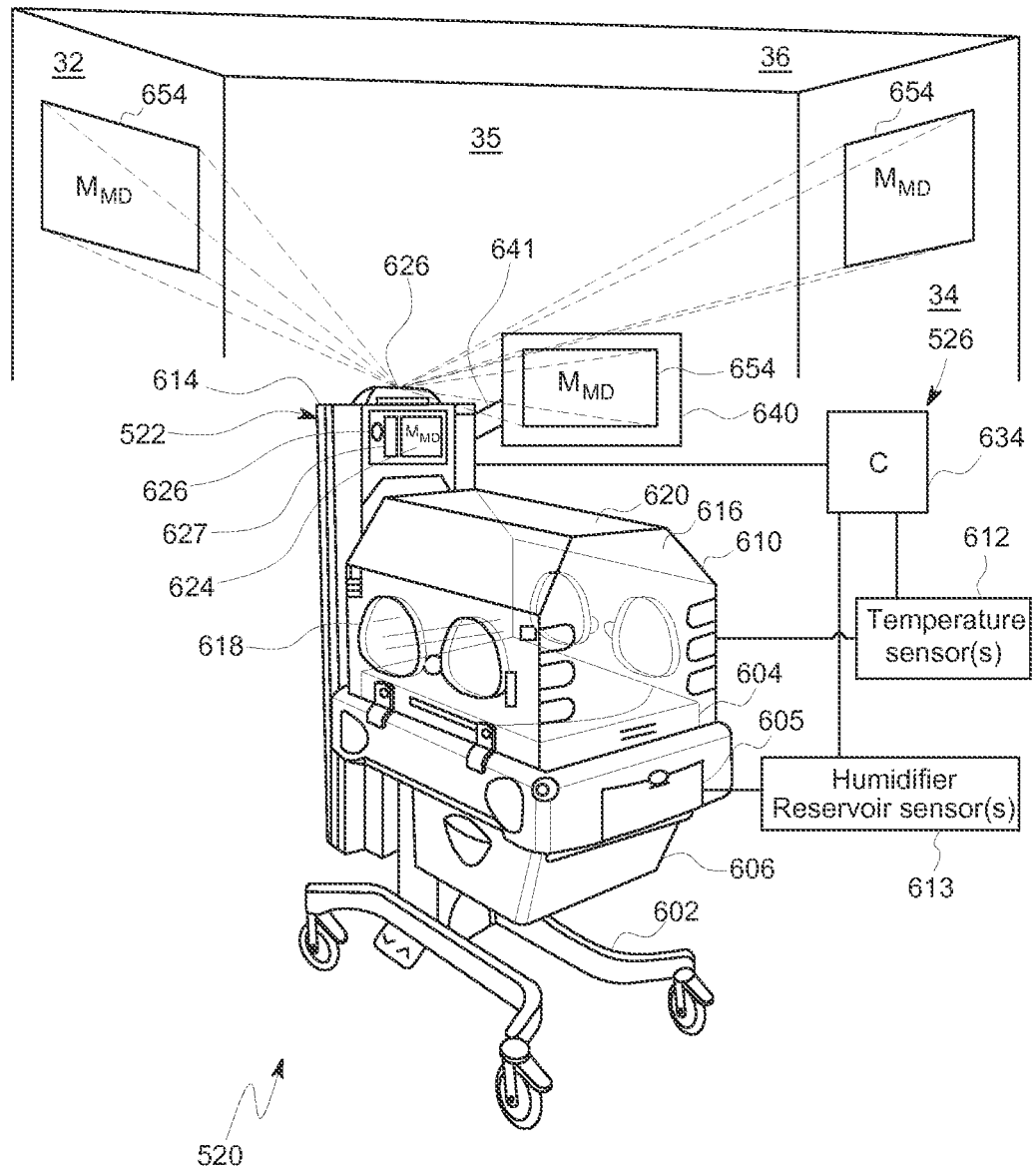
FIG. 6 is a perspective view of another example medical device visual management system.

FIG. 6 is a perspective view illustrating visual management system 520, another example implementation of visual management system 20. Visual management system 520 comprises a medical device comprising an infant care station 522 (also referred to as an incubator or warmer) and a message manager 526 incorporated as part of infant care station 522. For ease of illustration, internal electronic or computing components of medical device and 522 and message manager 526 are schematically illustrated external to infant care station 522.

Infant care station 522 is configured to provide a regulated or controlled neonatal infant microenvironment for one or more neonates or infants. Although infant care station 522 is illustrated as physically incorporating manager 526 as part of its electronics, in other implementations, infant care station 522 is independent of manager 526 (but for the provision projection devices 626, 627 carried by infant care station 522), wherein infant care station 522 communicates with manager 526 in a wired or wireless fashion.

Figure 7:
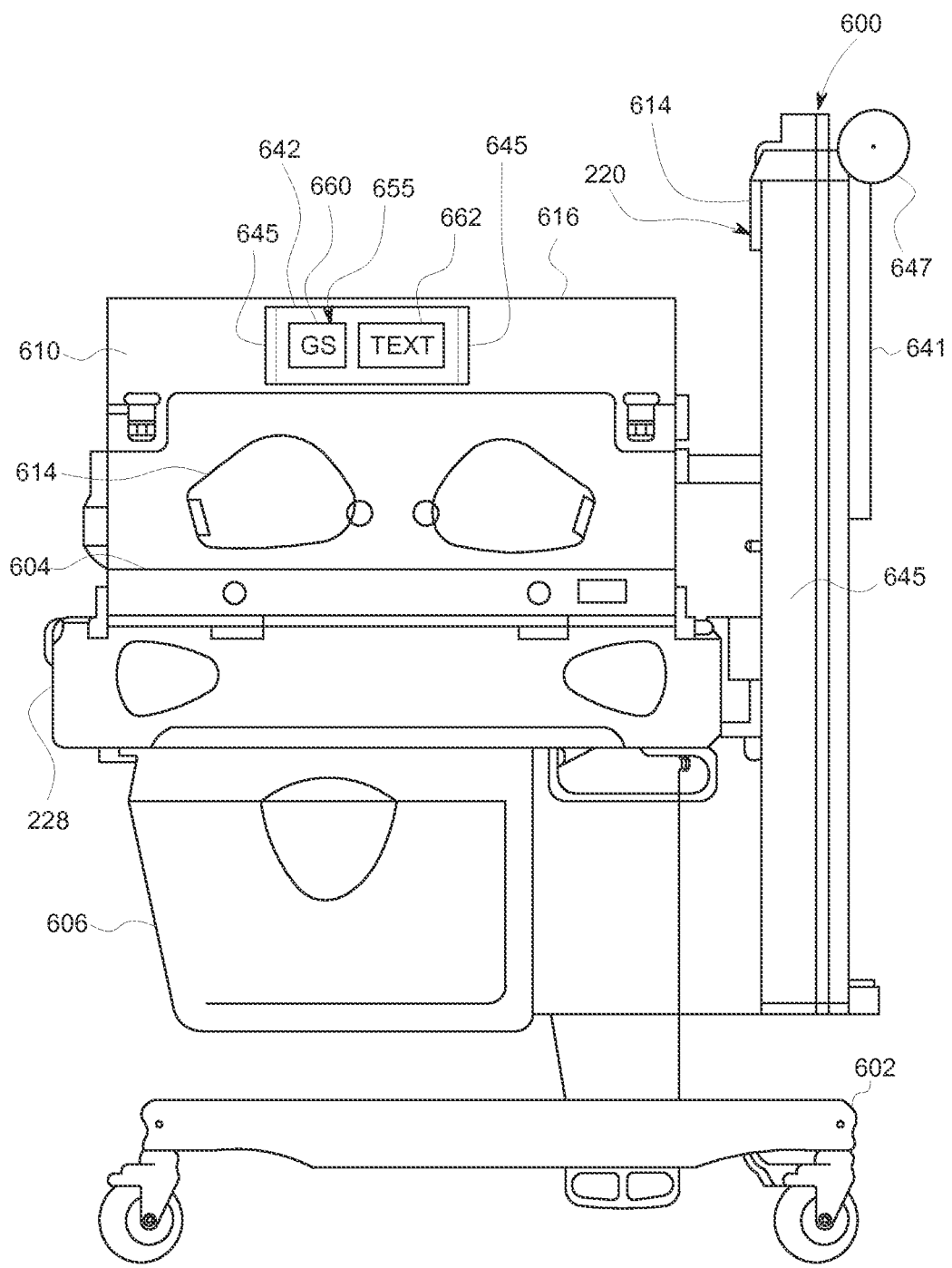
FIG. 7 is a right side view of the system of FIG. 6.

In the example illustrated, in addition to manager 526, infant care station 522 comprises base 602; bed 604; infant care station humidifier 605 having humidifier reservoir 606; hood 610; temperature sensors 612; humidifier reservoir sensors 613; control panel 614 providing display 624, auditory device 626 and input 627; auxiliary projection surface 640, auxiliary projection surface 641 and auxiliary chamber projection surface 642 (shown in FIGS. 7 and 8). Base 602 supports infant care station 522 at a selected height and facilitates transit of infant care station 522.

Bed 604 comprises a mattress or other structure upon which a neonatal infant may rest. In one implementation, bed 604 incorporates radiant infant care station heating components. In another implementation, radiant heating components may be provided along a side of the chamber provided by hood 610.

Humidifier 605 provides humidified air within chamber 616. Humidifier 605 draws evaporant, such as water, from reservoir 606. Humidifier reservoir 606 comprises a tank or other volume containing evaporant or water for infant care station humidifier 228. Although illustrated as being located below bed 230, reservoir 606 may be provided at other locations.

Hood 610 comprises a transparent housing extending about bed 604 to form a chamber 616 providing the micro neonatal environment for one or more infants. In the example illustrated, hood 610 includes a plurality of portholes 618 through which a healthcare provider may access the one or more infants within the chamber 616. In the example illustrated, hood 610 comprises a single structure movable as a unit. In other implementations, sidewalls of hood 610 may remain about bed 604 forming a crib, wherein the topmost portion or canopy 620 is separable from the sidewalls of hood 610 to access one or more infants.

Temperature sensors 612 comprise one or more sensors located to sense or detect the temperature within chamber 616. Humidifier reservoir sensors 613 comprise one or more sensors to sensor detect a level of the evaporant or water within reservoir 606. In one implementation, sensors 612 and 613 produce signals which are received by manager 526 and used by manager 526 as a basis for generating and projecting a message.

Control panel 614 facilitates the display and input of information with regard to infant care station 522. Control panel 614 comprises display 624, auditory device 626 and input 627. Display 624 comprises a display screen for presenting messages such as alarms, notifications, messages and data. In one implementation, display 64 may concurrently present the same information or message being projected by projection device 626. In one implementation, display 624 may present a message different from the message that is being projected. In one implementation, display 624 the different message presented by display 64 may include the message being projected as well as additional detailed information. Auditory device 626 comprises a speaker by which audible messages, such as information and alarms are audibly presented. In some implementations, visual management system 520 is operable in a mode in which audible alarms that would otherwise be produced by auditory device 626 are instead visibly presented by being projected onto a projecting surface so as to reduce undesirable noise levels in a healthcare environment. Input 627 is similar to input 324 described above with respect to systems 220 and 420.

Auxiliary projection surface 640 comprises a surface to receive an image of a message projected by projection device 626 through air external to the remainder of infant care station 522. Projection surface 640 comprises a large panel providing a large projection surface adjacent to infant care station 522 onto which projection device 626 projects an image, such as in circumstances where the room or other environment in which medical device or more 522 is located may not have an appropriate surface for receiving a projected image.

In the example illustrated, auxiliary projection surface 640 is suspended from control panel 614 by an arm 643. In one implementation, arm 643 is pivotally coupled to control panel 614, allowing projections surface 640 to be pivoted between various angles with respect to control panel 614. In one implementation, arm 643 is configured such that projection surface 640 may be pivoted out of the way, behind and parallel to a rear of control panel 614 when not in use. In other implementations, arm 643 and projection surface 640 may be omitted.

Auxiliary projection surface 641 comprises a flat white or otherwise reflective projection surface supported by rails 645 of at the head of infant care station 522. In the example illustrated, projection surface 641 faces away from chamber 616 to provide a projection service for other projection devices associated with other medical devices. In another implementation, projection surface 641 faces forward towards chamber 616, providing a surface for receiving and reflecting or otherwise making visible a projected image. In the example shown in FIG. 7, projection surface 641 is provided by a flexible and rollable or foldable panel which is resiliently biased by a torsion spring towards a rolled up position, allowing the panel to be retained with a catch in the extended, in use, position or retracted into a rolled cylinder 647.

Auxiliary chamber projection surface 642 comprises a projection surface provided along one of walls forming chamber 616 such as walls of hood 610. Projection surface 642 is configured to reflect or otherwise make visible image 655 (shown in FIG. 8) which is viewable upon projection surface 642. Because projection surface 642 makes viewable image 655 along a wall of chamber 616, a physician or care person may more easily view message 655 while viewing the infant within chamber 616 or while caring for the infant within chamber 616. For example, during surgical operations on an infant while the infant resides within chamber 616, a physician or nurse do not lift his or her head as much to view the information of message 655.

In the example illustrated, projection surface 642 comprises a colorless or white reflective card or panel configured to be removably retained in place along and adjacent to a wall of hood 610. In one implementation, hood 610 comprises a pair of channels, catches, grooves, clips or other retaining structures 645 which removably or releasably retain the panel providing projection surface 642 along the otherwise transparent wall of hood 610. As a result, a physician or care person may remove the panel providing projection surface 642 for greater view ability of one or more infants within chamber 616.

As shown by FIG. 8, auxiliary projection surface 642 is usable one or more operating modes for presenting image 655. In one mode of operation, projection surface 642 reflects or otherwise makes viewable image 655 projected from projector 626, wherein the image 655 is projected through air external to chamber 616 onto projection surface 642 which is external to the walls of hood 610. In another mode of operation, projection surface 642 reflects or otherwise makes visible image 655 being projected from auxiliary chamber projector 629, wherein image 655 is projected by auxiliary chamber projector 629 within chamber 616, through the transparent wall of hood 610, and onto the interior facing surface of projection surface 642.

Although projection surface 642 is illustrated as being removably or releasably retained on the outside of hood 610, in other implementations, projection surface 642 is alternatively retained on an inner surface of hood 610. In some implementations, projection service 642 is perfectly formed and fixed as part of hood 610. Although projection surface 642 is illustrated as being provided along angled surfaces oblique to horizontal and vertical directions, in other implementations, projection surface 642 alternatively provided along the top upwardly facing surface of what 610 or along vertical sidewalls of chamber 616. In some implementations, projection surface 642 baby concurrently utilized in both modes, wherein the same message 655 or different messages are concurrently projected onto the opposing faces of surface 642 by projection devices 626 and 629.

As shown by FIG. 7, message 655 comprises both graphic symbols 660 and text 662. Graphic symbols 660 communicate information independent of language, foregoing the possible need for translation. For example, in one implementation, graphic symbols 660 may comprise a projection of the graphic symbol of a humidifier showing the water level being low. In another implementation, graphic symbol 660 comprises a blue baby graphic which is presented in response to heart rate, respiratory rate and SPO2 being deemed by system 520 as presenting a concerning or dangerous situation. The projection of such a graphic symbol 660 could either be reserved to low level alarm conditions or be used for emergency alarms where image 655 comprises the graphic 660 and text 662 indicating the reason for the alert or providing instructions for addressing the alert. In one implementation, audible alarm make be concurrently presented along with graph 660 and/or text 662.

Manager 526 is similar to manager 226. Because manager 526 is incorporated as part of infant care station 522, manager 526 omits transmitters 320 and utilizes input 627 in place of input 324. In the example illustrated, controller 634 is similar to controller 334 described above with respect to systems 220 and 420 except that controller 634 additionally controls the operation of infant care station 522. In other implementations, controller 634 is independent of the controller controlling the operation of infant care station 522.

Similar to manager 226, manager 526 receives signals which are based upon parameters 50 associated with the use of infant care station 522. In the example illustrated, parameters 50 comprise sensed values pertaining to the current temperature within chamber 616 as detected by sensors 612 and the current level of evaporant or water in reservoir 606 as detected by sensors 613. In other implementations, managing 526 may receive signals based upon other parameters associated with use of infant care station 522. Based upon such signals, manager 226 generates control signals causing projection device 626 and/or projection device 629 to project at least one image of at least one message 654 onto projection surface 640, projection surface 642 and/or one or more of projection surfaces 32, 34, 36, 35 or 38 (shown in FIG. 1). As described above, manager 526 may generate control signals such that the particular projection surface chosen for receiving the projected message as well as the non-textual attributes of the message communicate an important or priority of the content of the message. As a result, a physician or other care person may more easily notice, read and appreciate the message, such as an alarm or other notification.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A visual management system for an infant care apparatus, wherein the infant care apparatus is at least one of an incubator and warmer, the system comprising:
    a projection device;
    a controller to generate control signals based upon parameters associated with use of the infant care apparatus, wherein the projection device projects a message comprising an alarm onto a surface, upon which the message is viewable, in response to the control signals.

2. The system of claim 1, wherein the message comprises alphanumeric symbols and wherein the controller is configured to indicate an importance of the message by generating control signals causing the projection device to vary non-textual attributes of the message based upon the importance of the message.

3. The system of claim 2, wherein the non-textual attribute is selected from a group of non-textual attributes consisting of: color, brightness, font, size and frequency of the alphanumeric symbols.

4. The system of claim 2, wherein the projection device is configured to select one of a plurality of available surfaces based on the importance of the message.

5. The system of claim 1, wherein the controller is configured to vary a brightness of the projection based upon at least one of a timer and a sensed ambient light.

6. The system of claim 1, wherein the control signals generated by the controller are additionally based upon sensed parameters associated with use of a medical device other than the infant care apparatus.

7. The system of claim 1, wherein the projection device is configured to project the message onto a surface remote from the infant care apparatus.

8. The system of claim 1 further comprising the infant care apparatus, wherein the infant care apparatus comprises a projection surface upon which the message projected by the projection device is viewable.

9. The system of claim 8, wherein the infant care apparatus comprises a chamber to receive a patient, wherein the projection surface extends along a wall of the chamber.

10. The system of claim 8, wherein the infant care apparatus comprises a bed and rails vertically extending above the bed, wherein the projection surface is supported by the rails.

11. The system of claim 1, wherein the projection device is configured to project the message through air external to the infant care apparatus.

12. The system of claim 1, wherein the projection device is configured to vary a location upon which the message is projected based upon an importance of the message.

13. The system of claim 1, wherein the infant care apparatus comprises an incubator and wherein the message is based upon a sensed level of water in a reservoir of the incubator.

14. The system of claim 1, wherein the message is based upon a sensed temperature of a patient.

15. The system of claim 1 further comprising a display screen, wherein the controller is configured to generate second control signals and wherein the display screen presents a second message in response to the second control signals, the second message comprising the message.

16. The system of claim 1, wherein the message has an alphanumeric character size of at least 1 inch.

17. The system of claim 1, wherein the message has an alphanumeric character size of at least 3 inches.

18. The system of claim 1, wherein the projection device is adjustable to project the message onto a selected one of a plurality of available surfaces.

19. The system of claim 1, wherein the surface comprises a projection surface of the infant care apparatus.

20. The system of claim 1, wherein the parameter comprises a sensed parameter sensed during operation of the infant care apparatus.

21. The system of claim 1 further comprising a sensor associated with the infant care apparatus to sense the parameter associated with use of the infant care apparatus.

22. The system of claim 1, wherein the parameter associated with use of the infant care apparatus comprises a current operational setting of the infant care apparatus.

23. The system of claim 1 further comprising the infant care apparatus, wherein the projection device is incorporated as part of the infant care apparatus.

24. The system of claim 1 further comprising a medical device other than the infant care apparatus, wherein the control signals generated by the controller are additionally based upon sensed parameters associated with use of the medical device.

25. The system of claim 24, wherein the projection device is incorporated as part of the infant care apparatus, wherein the system further comprises a second projection device incorporated as part of the medical device, wherein the projection device projects a first portion of the message through air external to the infant care apparatus and wherein the second projection device projects a second portion of the message through air external to the medical device.

26. The system of claim 24, wherein the message comprises a message portion applicable to each of the infant care apparatus and the medical device.

27. The system of claim 1, wherein the projection device is configured to project a first portion of the message onto the surface and a second portion of the message onto a different surface.

28. A method executed by a controller, the method comprising:
    receiving signals representing a parameter associated with use of an infant care apparatus, wherein the infant care apparatus is at least one of an incubator and warmer; and
    projecting a message comprising an alarm onto a surface upon which the message is viewable, the message based upon the parameter.

29. An apparatus comprising:
    a non-transitory computer-readable medium containing code configured to direct a processor to:

receive signals representing a parameter associated with use of an infant care apparatus, wherein the infant care apparatus is at least one of an incubator and a warmer, and project a message comprising an alarm onto a surface upon which the message is viewable, the message based upon the parameter.

\* \* \* \* \*